United States Patent [19]
Burnie et al.

[11] Patent Number: 5,288,639
[45] Date of Patent: Feb. 22, 1994

[54] FUNGAL STRESS PROTEINS

[75] Inventors: James P. Burnie; Ruth C. Matthews, both of Wilmslow, United Kingdom

[73] Assignee: The Victoria University of Manchester, Manchester, England

[21] Appl. No.: 663,897

[22] PCT Filed: Jul. 2, 1990

[86] PCT No.: PCT/GB90/01021
§ 371 Date: Mar. 14, 1991
§ 102(e) Date: Mar. 14, 1991

[87] PCT Pub. No.: WO91/00351
PCT Pub. Date: Jan. 10, 1991

[30] Foreign Application Priority Data
Jun. 30, 1989 [GB] United Kingdom ............ 8915019.7

[51] Int. Cl.$^5$ .................... C12N 15/31; C12N 15/63; C07K 5/00; C07K 7/00; C07K 13/00
[52] U.S. Cl. ............................. 435/320.1; 530/300; 530/327; 530/328; 530/329; 530/330; 530/350; 530/371; 530/806; 530/823; 435/921; 435/922; 435/924; 536/23.74; 935/9; 935/11; 935/12
[58] Field of Search ............... 530/371, 330, 329, 328, 530/300, 350; 536/327, 27, 23.74; 435/320.1, 69.1, 69.3, 921, 922, 924; 935/9, 11, 12

[56] References Cited

U.S. PATENT DOCUMENTS 4,732,852 3/1988 Cohen et al. .................... 435/68

FOREIGN PATENT DOCUMENTS 0145333 6/1985 European Pat. Off. .
8605400 9/1986 World Int. Prop. O. .

OTHER PUBLICATIONS

Matthews et al., "Immunoblot Analysis of the Serological Response in Systemic Candidosis", Lancet, pp. 1415–1418, Dec. 22–29, 1984.

Matthews et al., "Isolation of Immunodominant Antigens from Sera of Patients with Systemic Candidiasis and Characterization of Serological Response to Candida Albicans" Journal of Clinical Microbiol., 25(2):230–237, 1987.

Matthews et al., "Characterization and Cellular Localization of Immunodominant 47 KDa Antigen of Candida Albicans", Journal of Medical Microbiology, 27:227–232, 1988.

Neale et al., "The Immunochemical Characterization of Circulating Immune Complex Constituents in Candida Albicans Osteomyelitis by Isoelectric Focusing, Immunoblot and Immunoprint", Aust. NZ. J. Med., 17:201–208, 1987.

Matthews, et al. 1989 FEMS Microbiology Letters 60:25–30.

Burnie, J. P. et al. 1985 Lancet No. 8438 p. 1155.

Young, R. A. et al. 1983 Proc. Nat. Acad. Sci., U.S.A. 80:1194–1198.

Farrelly, T. W. et al. 1984 Jour. Biol. Chem. 259:5745–5751.

Primary Examiner—Robert A. Wax
Assistant Examiner—Gabriele E. Bugaisky
Attorney, Agent, or Firm—Cushman, Darby & Cushman

[57] ABSTRACT

A polypeptide sequence from *Candida albicans* is described which has significant sequence homology with known stress proteins from other organisms, particularly the heat shock protein hsp 90 of *Sacchromyces cerevisiae*. Corresponding DNA sequences are also described, together with antibodies raised against fragments of the sequence. The polypeptide and DNA sequences and antibodies provide separate means for the diagnosis and/or treatment of fungal, particularly Candida, infections.

11 Claims, 7 Drawing Sheets

```
           10         20         30         40         50         60
CA-orf  EFRAILFVPKRAPFDAFESKKKKNNIKLYVRRVFITDDAEELIPEWLSFIKGVVDSEDLP
        ::::::::: ::::::: ::::::::::::::::::::: :: ::::::::::: :::::::
SCHS90  EFRAILFIPKRAPFDLFESKKKKNNIKLYVRRVFITDEAEDLIPEWLSFVKGVVDSEDLP
           320        330        340        350        360        370

70         80         90        100        110        120
CA-orf  LNLSREMLQQNKILKVIRKNIVKKMIETFNEISEDQEQFNQFYTAFSKNIKLGIHEDAQN
        ::::::::::::: :::::::::::: ::::::: :::::: ::::::::::: :::::
SCHS90  LNLSREMLQQNKIMKVIRKNIVKKLIEAFNEIAEDSEQFEKFYSAFSKNIKLGVHEDTQN
           380        390        400        410        420        430

130        140        150        160        170        180
CA-orf  RQSLAKLLRFYSTKSSEEMTSLSDYVTRMPEHQKNIYYITGESIKAVEKSPFLDALKAKN
        : : ::::: : ::::  : :: :::::::::::::::::::::::::::::::::::::
SCHS90  RAALAKLLRYNSTKSVDELTSLTDYVTRMPEHQKNIYYITGESLKAVEKSPFLDALKAKN
           440        450        460        470        480        490

190        200        210        220        230        240
CA-orf  FEVLFMVDPIDEYAMTQLKEFEDKKLVDITKDFELEESDEEKAAREKEIKEYEPLTKALK
        ::::: ::::::::: ::::::: : :::::::::::: :::::.::::::::::::::
SCHS90  FEVLFLTDPIDEYAFTQLKEFEGKTLVDITKDFELEETDEEKAEREKEIKEYEPLTKALK
           500        510        520        530        540        550

250        260        270        280        290        300
CA-orf  DILGDQVEKVVVSYKLVDAPAAIRTGQFGWSANMERIMKAQALRDTTMSSYMSSKKTFEI
         :::::::::::::::: ::::::::::::::::::::::::::: :::::::::::::
SCHS90  EILGDQVEKVVVSYKLLDAPAAIRTGQFGWSANMERIMKAQALRDSSMSSYMSSKKTFEI
           560        570        580        590        600        610

310        320        330        340        350        360
CA-orf  SPSSPIIKELKKKVETGAEDKTVKDLTTLLFDTALLTSGFTLDEPSNFAHRINRLIALG
        ::.:::::::::: :: :: ::::::::: :: ::::::::: ::::.: :::::: :
SCHS90  SPKSPIIKELKKRVDEGGAQDKTVKDLTKLLYETALLTSGFSLDEPTSFASRINRLISLG
           620        630        640        650        660        670

370        380        390
CA-orf  LNIDDDSEETAVEPEATTTASTDEPAGESAMEEVD*
        ::: ::  ::: :: ::  ::  : : ::::::::
SCHS90  LNIDED-EETETAPEASTAAPVEEVPADTEMEEVD*
           680        690        700
```

FIG.3

FUNGAL STRESS PROTEINS

FIELD OF THE INVENTION

This invention relates to fungal stress proteins, to corresponding DNA sequences, to fungal stress protein inhibitors and to their use in medicine and for diagnosis.

BACKGROUND TO THE INVENTION

Environmental stress can induce an increase in the rate of synthesis of so-called heat shock, or stress, proteins in both procaryotic and eucaryotic cells [see for example Schlesinger et al (eds) in Heat Shock from Bacteria to Man, Cold Spring Harbor Laboratory, Cold Spring Harbor, N.Y. (1972)]. Although the function of stress proteins has yet to be finally resolved, some have been reported to participate in assembly and structural stabilisation of cerain cellular and viral proteins, and their presence at high concentration may have an additional stabilising effect during exposure to adverse conditions.

Many pathogenic organisms have been shown to produce stress proteins [see for example Young D, et al, Proc. Natl. Acad. Sci. USA 85, 4267-4270 (1988)]. The proteins are thought to be produced in response to the stress of infection to help protect the invading pathogen. Thus, for example, the ability to produce stress proteins has been implicated in the survival of bacterial pathogens within macrophages [Christmas, M. F. et al, Cell, 41, 753-762 (1985) and Morgan, R. W. et al, Proc. Natl. Acad. Sci. USA, 83, 8059-8063, (1986)].

It has been suggested that the presence of stress proteins in a variety of human pathogens indicates that the stress response is a general component of infections, and that stress proteins should be considered among candidates for subunit vaccines [Young, D. et al, ibid].

Candida albicans is, medically, the most important of the human fungal pathogens. Systemic candidiasis (candidosis) is an increasingly common cause of death amongst immunocompromised and debilitated patients, with a mortality of over 70% [Gold, J. W. M., Am. J. Med. 76, 458-463, (1984)]; while oral candidiasis is a frequent early manifestation of the acquired immunodeficiency syndrome [Klein, R. S. et al, N. Engl. J. Med. 311, 354-357, (1984)]. Candidiasis is difficult to diagnose, and is not easy to treat, mainly since the usual method of treatment involves use of amphotericin B, which is itself highly toxic. A need therefore exists in the diagnosis and treatment of Candida infections for more sensitive diagnostic methods and treatment which has less toxic side effects.

A number of Candida antigens have been detected in the sera of patients with systemic candidiasis [Matthews, R. C. et al, J. Clin. Microbiol. 25, 230-237 (1987)]. One of these, with a relative molecular mass of approximately 47 kilodaltons (47 kd) is an immunodominant antigen which has been reported by four independent groups [Matthews R. C., et al Lancet ii, 1415-1418 (1984); Au-Young, JK et al, Diagn. Microbiol. Infect. Dis., 3, 419-432, (1985); Neale T. J., et al, Aust. N. Z. J. Med., 17, 201-209 (1987); and Ferreira R. P. et al, J. Clin. Microbiol. 28, 1075-1078 (1990)]. This 47 Kd antigen is distinct from the 48-52 Kd antigen described by Strockbine et al [Strockbine N. A. et al Infect. Immun. 43, 715-721 (1984)] for two reasons:

(1) monoclonal antibodies raised against the 48-52 Kd antigen cross-react with antigens at 120-135 Kd and 35-38 Kd [Strockbine N. A. et al, Infect Immun 43, 1012-18 (1984); Buckley H. R., et al U.S. Pat. No. 4670382 (1987)] and (2) the 48-52 Kd antigen it is an enolase [Safranek W. W. and Buckley H. R., Second Conference on Candida and Candidiasis, Abstract A7 (1990). In contrast, antibody to the 47 Kd antigen cross-reacts with an antigen at about 92 Kd (see below). An immundominant C. albicans antigen of 54.3 Kd (range 48.9 to 59.7 Kd) was described by Greenfield R. A., and Jones J. M., in Infect. Immun. 34, 469-477 (1981).

SUMMARY OF THE INVENTION

We have now been able to clone and express part of the DNA sequence encoding the 47 Kd antigen, and in doing so we have surprisingly discovered a polypeptide sequence which has significant sequence homology with known stress proteins from other organisms, particularly the heat shock protein hsp 90 of Saccharomyces cerevisiae [Farrelly F. W. and Finkelstein D. B., J. Biol. Chem. 259, 5745-5751 (1984)]. In Saccharomyces two genes exist, hsp 90 and hsc 90, coding for 98% homologous proteins [Finkelstein D. B. and Farrelly F. W., Fed. Proc. 43, 1499 Abstr. 482 (1984)]. Either of the genes can be deleted without affecting cell viability, however, deletion of both genes is lethal. The separate genes produce a constitutive and an inductible form [D. Finkelstein, personal communication cited in Lindquist S. Ann. Rev. Biochem. 55, 1151-91 (1986)].

We can also now suggest that there are two forms of a C. albicans stress or heat shock protein hsp 90. Thus a 47 Kd breakdown product occurs on immunoblots of C. albicans grown at 37° C. or 23° C. whereas a 92 Kd antigen only appears at 37° C. This suggests a heat-inducible, stable hsp 90 is produced at 37° C., but not at 23° C., whereas a more labile hsp 90 occurs at 23° C. which breaks down to the 47 Kd subcomponent under denaturing conditions. We have used this discovery to develop means for the improved diagnosis and treatment of candida infections and related fungal disease.

Thus according to one aspect of the invention we provide a fungal stress protein having an amino acid sequence which includes at least the sequence of formula (1):

```
          10        20        30              (1)
     EFRAILFVPKRAPFDAFESKKKKNNIKLYV 40        50        60
         RRVFITDDAEELIPEWLSFIKGVVDSEDLP 70        80        90
     LNLSREMLQQNKILKVIRKNIVKKMIEIFN 100       110       120
            EISEDQEQFNQFYTAFSKNIKLGIHEDAQN 130       140       150
     RQSLAKLLRFYSTKSSEEMTSLSDYVTRMP 160       170       180
               EHQKNIYYITGESIKAVEKSPFLDALKAKN 190       200       210
     FEVLFMVDPIDEYAMTQLKEFEDKKLVDIT 220       230       240
                KDFELEESDEEKAAREKEIKEYEPLTKALK
```

```
              250         260         270
DILGDQVEKVVVSYKLVDAPAAIRTGQFGW 280         290         300
           SANMERIMKAQALRDTTMSSYMSSKKTFEI 310         320         330
SPSSPIIKELKKKVETDGAEDKTVKDLTTL 340         350         360
                LFDTALLTSGFTLDEPSNFAHRINRLIALG 370         380         390
LNIDDDSEETAVEPEATTTASTDEPAGESAMEEVD*
``` or a fragment thereof, or an analogue thereof.

The single letters in formula (1) are each to be understood to represent a separate amino acid, and each is the conventional single letter symbol used for amino acids.

The stress protein according to the invention may be of fungal origin and may be obtainable, for example, from strains belonging to the genera Candida, for example Candida parapsilosis, Candida krusei and, in particular, Candida albicans and Candida tropicalis; Cryptococcus, for example Cryptococcus neoformans; Histoplasma, for example Histoplasma capsulatum, and related yeasts; and Aspergillus, for example Aspergillus fumigatus and related filamentous fungi.

Particular fragments of a stress protein according to the invention include any peptide epitopes, for example of a few amino acids or analogues thereof. Examples of such epitopes include STDEPAGESA, LSREM, LKVIRK and LKVIRKNIVKKMIE. Peptides of this type may be synthesised using conventional liquid or solid phase peptide synthesis techniques.

Analogues of a stress protein according to the invention include those proteins wherein one or more amino acids in the sequence of formula (1) is replaced by another amino acid, providing that the overall functionality of the protein is conserved.

A stress protein according to the invention may be obtained in a purified form, and thus according to a further aspect of the invention we provide a substantially pure fungal stress protein having an amino acid sequence which includes at least the sequence of formula (1), and analogues thereof.

The term substantially pure is intended to mean that the stress protein according to the invention is free from other proteins of fungal origin. In the various aspects of the invention described hereinafter it is to be understand that a reference to the fungal stress protein also includes substantially pure preparations of the protein.

In a further aspect the invention particularly provides a recombinant fungal stress protein having an amino acid sequence which includes at least the sequence of formula (1) or a fragment thereof, or an analogue thereof.

A stress protein according to the invention may be further characterised by one or more of the following features:

(1) it has an isoelectric point (pI) in a range around pI 4 to pI 5;

(2) it is an immunodominant conserved antigen;

(3) patients recovering from systemic candidiasis seroconvert to the stress protein;

(4) patients with acquired immunodeficiency syndrome have antibody to the stress protein;

(5) antibody raised against the stress protein cross-reacts with both the 47 kilodalton and/or approximately 92 kilodalton antigens of Candida albicans using affinity-purified polyclonal monospecific antibody against the 47 kilodalton antigen.

A stress protein according to the invention has a number of uses. Thus, for example, the protein may form the basis of a diagnostic test for fungal infection, for example an immunological test such as an enzyme-linked immunosorbent assay, a radioimmunoassay or a latex aggulutination assay, essentially to determine whether antibodies specific for the protein are present in an organism.

In another use, the stress protein according to the invention may be employed, using conventional techniques, for screening to obtain activity inhibiting agents for use in the treatment of fungal infections. Such a screening method forms a further aspect of the invention.

In a further use, the stress protein according to the invention is particularly well suited for the generation of antibodies. Thus according to a further aspect of the invention we provide a fungal stress protein having an amino acid sequence which includes at least the sequence of formula (1) or a fragment thereof or an analogue thereof, for use as an immunogen.

Standard immunological techniques may be employed with the stress protein in order to use it as an immunogen. Thus, for, example, any suitable host may be injected with the protein and the serum collected to yield the desired polyclonal anti-stress protein antibody after purification and/or concentration. Prior to injection of the host the stress protein may be formulated in a suitable vehicle and thus according to a further aspect of the invention we provide a composition comprising a fungal stress protein having an amino acid sequence which includes at least the sequence of formula (1) or an analogue thereof together with one or more pharmaceutically acceptable excipients.

For purification of any anti-stress protein antibody, use may be made of affinity chromatography employing an immobilised stress protein of the invention as the affinity medium. This according to another aspect of the invention we provide a fungal stress protein having an amino acid sequence which includes at least the sequence of formula (1), or a part thereof or an analogue thereof, covalently bound to an insoluble support.

The use of the stress proteins according to the invention as immunogens for the production of antibodies generates one type of inhibitor of the action of the protein. Generally, inhibitors of the stress proteins are potentially useful in the diagnosis, and in particular the treatment, of fungal infections and provide a further feature of the invention. Inhibitors include any antagonists of the action of the stress proteins or agents which prevent their production, and in particular include those which may be used in the treatment of fungal infections. Suitable inhibitors include for example pharmaceutical reagents, including antibodies, and chemical analogues of the stress proteins to antagonise the action of the stress protein, and anti-sense RNA and DNA to prevent production of the stress protein. Suitable inhibitors may be determined using appropriate screens, for example by measuring the ability of a potential inhibitor to antagonise the action of, or prevent the production of a stress protein according to the invention or a fragment thereof, or an analogue thereof, in a test model for example an animal model such as the mouse model described in the Examples hereinafter.

According to a further aspect of the invention we provide an inhibitor of a fungal stress protein, said protein having an amino acid sequence which includes at least the sequence of formula (1) or a fragment thereof or an analogue thereof, for use in the diagnosis or treatment of fungal infections.

Inhibitors may be used either alone or where appropriate in combination with other pharmaceutical agents, for example, other anti-fungal agents, such as amphotericin or flucytosine.

One particularly useful group of inhibitors according to this aspect of the invention are antibodies capable of recognising and binding to the stress proteins.

Thus, according to yet another aspect of the invention we provide an antibody specific for one or more epitopes of a fungal stress protein having an amino acid sequence which includes at least the sequence of formula (1) or a fragment thereof or an analogue thereof.

The antibody may be a whole antibody or an antigen binding fragment thereof and may in general belong to any immunoglobulin class. Thus, for example, it may be an immunoglobulin M antibody or, in particular, an immunoglobulin G antibody. The antibody or fragment may be of animal, for example mammalian origin and may be for example of murine, rat or human origin. It may be a natural antibody or a fragment thereof, or, if desired, a recombinant antibody or antibody fragment, i.e. an antibody or antibody fragment which has been produced using recombinant DNA techniques.

Particular recombinant antibodies or antibody fragments include, (1) those having an antigen binding site at least part of which is derived from a different antibody, for example those in which the hypervariable or complementarity determining regions of one antibody have been grafted into the variable framework regions of a second, different antibody (as described in European Patent Specification No. 239400); (2) recombinant antibodies or fragments wherein non-Fv sequences have been substituted by non-Fv sequences from other, different antibodies (as described in European Patent Specifications Nos. 171496, 173494 and 194276); or (3) recombinant antibodies or fragments possessing substantially the structure of a natural immunoglobulin but wherein the hinge region has a different number of cysteine residues from that found in the natural immunoglobulin, or wherein one or more cysteine residues in a surface pocket of the recombinant antibody or fragment is in the place of another amino acid residue present in the natural immunoglobulin (as described in International Patent Applications Nos. PCT/GB 88/00730 and PCT/GB 88/00729 respectively).

The antibody or antibody fragment may be of polyclonal, or preferably, monoclonal origin. It may be specific for a number of epitopes associated with the stress protein but it is preferably specific for one.

Antigen binding antibody fragments include for example fragments derived by proteolytic cleavage of a whole antibody, such as F(ab')$_2$, Fab' or Fab fragments, or fragments obtained by recombinant DNA techniques, for example Fv fragments (as described in International Patent Application No. PCT/GB 88/00747).

The antibodies according to the invention may be prepared using well-known immunological techniques employing the stress protein as antigen. Thus, for example, any suitable host may be injected with the stress protein and the serum collected to yield the desired polyclonal antibody after appropriate purification and/or concentration (for example by affinity chromatography using the immobilised stress protein as the affinity medium). Alternatively splenocytes or lymphocytes may be recovered from the stress protein injected host and immortalised using for example the method of Kohler et al, Eur. J. Immunol. 6, 511, (1976), the resulting cells being segregated to obtain a single genetic line producing monoclonal anti-fungal stress proteins. Antibody fragments may be produced using conventional techniques, for example by enzymatic digestion, e.g. with pepsin [Parham, J. Immunol, 131, 2895 (1983)] or papain [Lamoyi and Nisonoff, J. Immunol. Meth., 56, 235, (1983)]. Where it is desired to produce recombinant antibodies according to the invention these may be produced using for example the methods described in European Patent Specifications Nos. 171496, 173494, 194276 and 239400.

Antibodies according to the invention may be labelled with a detectable label or may be conjugated with effector molecule for example a drug e.g. an anti-fungal agent such as amphotericin B or flucytosine or a toxin, such as ricin, or an enzyme, using conventional procedures and the invention extends to such labelled antibodies or antibody conjugates.

the antibodies according to the invention have a diagnostic and/or therapeutic use. Thus for diagnostic use the antibodies may be employed to detect whether the stress protein is present in a host organism, to confirm whether the host has a particular fungal infection, for example an infection due to a Candida, Cryptococcus, Histoplasma or Aspergillus organism, for example in the diagnosis of fungal abcesses, especially hepatic Candidiasis, and/or to monitor the progress of therapeutic treatment of such infections. Diagnostic methods of this type form a further aspect of the invention and may generally employ standard techniques, for example immunological methods such as enzyme-linked immunosorbent methods, radioimmuno-methods, lates agglutination methods or immunoblotting methods.

Antibodies according to the invention also have a therapeutic use in the treatment of fungal infections, for example those just described and may be used alone or conjugated to an effector molecule, in the latter case to target the effector molecule, e.g. an anti-fungal agent such as amphotericin B or flucytosine, to the infecting organism. For therapeutic use the antibody may be formulated in accordance with conventional procedures, for example with a pharmaceutically acceptable carrier or excipient, e.g. isotonic saline for administration at an appropriate dosage, depending on the nature of the infection to be treated and the age and condition of the patient.

If desired, mixtures of antibodies may be used for diagnosis or treatment, for example mixtures of two or more antibodies recognising different epitopes of a fungal stress protein according to the invention, and/or mixtures of antibodies of a different class, e.g. mixtures of IgG and IgM antibodies recognising the same or different epitope(s) of a fungal stress protein of the invention.

The stress proteins according to the invention may be prepared by a variety of processes, for example by protein fractionation from appropriate fungal cell extracts, using conventional separation techniques such as ion exchange and gel chromatography and electrophoresis, or by the use of recombinant DNA techniques, as more particularly described in the Examples hereinafter. The use of recombinant DNA techniques is particularly suitable for preparing substantially pure stress proteins according to the invention.

Thus according to a further aspect of the invention we provide a process for the production of a fungal stress protein having an amino acid sequence which includes at least the sequence of formula (1) or an analogue thereof, comprising the steps of (1) culturing a host organism transformed with a vector including a tion. Desirably the fusion protein includes a protein produced at a high level by a transformed host organism. Suitable such proteins include at least a portion of a chloramphenicol acetyltransferase (CAT) protein or, preferably at least a portion of the β-galactosidase protein.

According to a still further aspect of the invention we provide a DNA sequence coding for a fungal stress protein having substantially the nucleotide sequence of formula (2):

```
GAATTCAGAGCTATCTTGTTTGTTCCAAAGAGAGCTCCATTTGATGCCTTTGAATCCAAG
    10        20        30        40        50        60

AAGAAGAAGAACAACATCAAATTATACGTCCGTAGAGTGTTTATCACTGATGATGCTGAA
    70        80        90       100       110       120

GAGTTGAATCCAGAATGGTTAAGTTTCATCAAGGGGGTTGTCGATTCCGAAGACTTGCCA
   130       140       150       160       170       180

TTGAACTTGTCCAGAGAAATGTTGCAACAAAACAAGATTTTGAAAGTTATCAGAAAGAAC
   190       200       210       220       230       240

ATTGTCAAAAGATGATTGAAACTTTCAATGAAATCTCTGAAGACCAAGAGCAATTCAAC
   250       260       270       280       290       300

CAATTCTACACTGCTTTCTCCAAGAACAYCAAAYYHHHYAYYCAYHAAHAYHCYCAAAAC
   310       320       330       340       350       360

AGACAATCTTTGGCTAAATTGTTGAGATTCTACTCTACCAAATCTTCTGAAGAAATGACT
   370       380       390       400       410       420

TCCTTGTCTGACTACGTTACTAGAATGCCAGAACACCAAAAGAATATCTACTACATCACT
   430       440       450       460       470       480

GGTGAATCCATCAAAGCCGTTGAAAAATCACCATTCTTGGATGCCTTGAAAGCTAAGAAC
   490       500       510       520       530       540

TTTGAAGTCTTGTTCATGGTGGATCCAATCGATGAATATGCCATGACTCAATTGAAGGAA
   550       560       570       580       590       600

TTTGAAGACAAGAAATTGGTTGATATTACCAAAGACTTTGAATTGGAAGAAAGTGACGAA
   610       620       630       640       650       660

GAAAAAGCTGCTAGAGAAAAGGAAATCAAAGAATACGAACCATTGACCAAAGCTTTGAAA
   670       680       690       700       710       720

GATATTCTTGGTGSTCAAGTTGAAAAAGTTGTTGTTTCCTACAAACTTGTTGATGCTCCA
   730       740       750       760       770       780

GCTGCCATTSGAACTGGTCAATTTGGTTGGTCTGCCAATATGGAAAGAATCATGAAGGCT
   790       800       810       820       830       840

CAAGCTTTGAGAGACACCACCATGTCTTCTTACATGTCCTCTAAGAAGACCTTTGAAATT
   850       860       870       880       890       900

TCTCCATCTTCCCCAATTATCAAGGAATTCAAGAAGAAAGTTGAAACCGATGGAGCTGAA
   910       920       930       940       950       960

GACAAGACCGTTAAGGACTTGACCACTTTGTTGTTTGATACTGCATTGTTGACTTCTGGT
   970       980       990      1000      1010      1020

TTCACCTTGGACGAACCATCCAACTTTGCCCACAGAATTAACAGATTGATTGCCTTGGGA
  1030      1040      1050      1060      1070      1080

TTGAATATTGACGATGATTCAGAAGAAACTGCTATTGAACCTGAAGCTACTACTACTGCC
  1090      1100      1110      1120      1130      1140

TCAACTGACGAACCAGCTGGAGAATCTGCTATGGAAGAAGTTGATTAAACACCAGAAGGG
  1150      1160      1170      1180      1190      1200
``` gene coding for a precursor of said protein, (2) cleaving said precursor to produce said protein and (3) recovering said protein.

Preferably the precursor cleaved in this aspect of the invention is a fusion protein comprising at least a portion of a protein produced in a transformed host organism and at least the amino acid sequence of formula (1). Such fusion proteins form a further aspect of the invention and homologues thereof.

DNA with this sequence may be obtained from fungal genomic DNA as described in the Examples hereinafter.

The DNA sequence according to this aspect of the invention may be incorporated in an expression vector using conventional techniques. Thus in a further aspect of the invention we provide an expression vector including substantially a DNA sequence of formula (2) or a homologue thereof.

The vector may be adapted for use in a given host cell by the provision of suitable selectable markers, promoters and other control regions as appropriate. Host cells transformed with such vectors form a further aspect of the invention. Suitable host organisms include bacteria (e.g. *E. coli*), and mammalian cells in tissue culture.

The DNA sequence of formula (2) may also be used to design DNA probes for use in identifying the presence of fungal stress proteins in the infected state and the invention extends to such DNA probes. Such probes may also be of use for detecting circulating fungal nucleic acids, for example using a polymerase chain reaction, as a method of diagnosing fungal infections. The probe may be synthesised using conventional techniques and may be immobilised on a solid phase, capable of immobilisation on a solid phase, or may be labelled with a detectable label.

It will also be appreciated that by suitable epitope mapping, using conventional procedures, for example as described in Example 2 hereinafter peptide fragments of the stress proteins may be identified which can be chemically synthesised. Synthetic peptide antigens of this type may be used to raise antibodies for use in diagnosis and/or therapy, as previously described, or to produce antiseras, e.g. non-specific polyclonal antisera, for use as a vaccine, and as discussed above form a further aspect of the invention.

BRIEF DESCRIPTION OF THE DRAWINGS

In the following description various embodiments of the present invention are described with reference to the accompanying drawings in which:

FIG. 2B shows immunoblots of recombinant lysogen CA-1 probed with monoclonal antibody against β-galactosidase.

FIG. 3 is a comparison of the predicted amino acid sequence of the *C.albicans* open reading frame (CA-orf) with *S.cerevisae* hsp90.

DESCRIPTION OF SPECIFIC EMBODIMENTS

Figure 1:
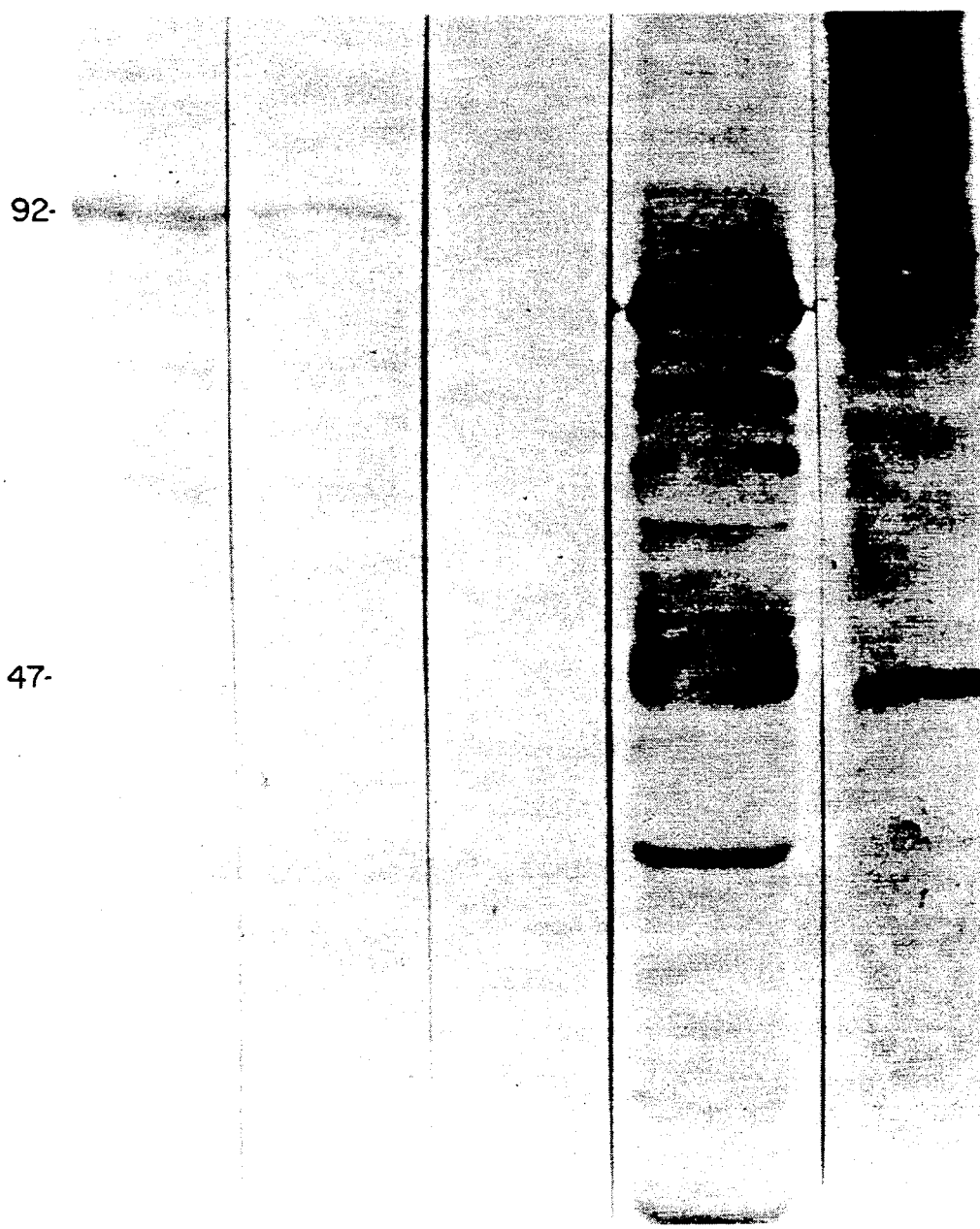
FIG. 1 shows immunoblots of *C.albicans* probed with antigen-selected antibodies.

The following Examples illustrate the invention, in which Example 1 describes the preparation of a stress protein according to the invention; Example 2 describes the epitope mapping of a stress protein according to the invention, the preparation of particular peptide epitopes and their use in detecting Candida infections; Example 3 describes the preparation of a monoclonal antibody against a particular epitope; and Example 4 describes the use of a particular monoclonal antibody [raised against an epitope of a stress protein according to the invention] to protect against Candida infection in mice.

EXAMPLE 1

Strain and Culture Conditions

A fully characterised strain of *C. albicans* (serotype A, morophotype A1, biotype 157), responsible for the first London hospital outbreak of systemic candidiasis [Burnie, J. P. et al, Brit. Med. J., 290, 746-748 (1985)] was grown at 37° C. overnight with aeration in 2% glucose broth.

Preparation and Screening of Genomic Library

Genomic DNA was prepared by the method of Wills et al [J. Bacteriol. 157, 918-924 (1984)], as modified by Scherer and Stevens [Proc. Natn. Acad. Sci. USA 85, 1452-1456, (1988)]. It was partially digested with EcoRI and fragments 2-7 kilobase pairs long were cloned into the unique EcoRI restriction enzyme site of the expression vector lambda gt 11 [Huynh, T. et al in DNA Cloning Techniques: A Practical Approach, Glover, D. Ed, pp. 49-78, IRL Press, Oxford (1985), and Young, R. A. and Davis, P. W., Proc. Natn. Acad. Sci. USA 80, 1194-1198, (1983)]. The library was screened with rabbit antiserum raised against soluble candidal antigens produced by fragmenting *C. albicans* yeast cells at −20° C. in an X-press [Matthews, R. C. et al, J. Clin. Microbiol. 25, 230-237 (1987)-(1)]. Immunoblotting against *C.albicans*, as previously described [Matthews, R. C. et al, Lancet ii, 1415-1418, (1984)-(2); Matthews, R. C. et al J. Clin. Microbiol. ibid], confirmed that the antiserum contained high titre antibody to many antigens including the 47 KD antigen. Five positive clones were identified by screening approximately $10^5$ plaques.

Characterisation of Positive Clones

The epitope expressed by each of the positive clones was identified by antigen-selection as described by Lyon et al [Proc. Natn. Acad. Sci. USA, 83, 2989-2993, (1986)]. For this the polyspecific rabbit antiserum was affinity purified against positive recombinant plaques and the bound antibody, eluted with glycine buffer pH 2.8, screened against an immunoblot of *C.albicans* [Matthews, R. C. et al, (1), (2) ibid]. Lysogens were prepared in *E.coli* Y1089 as described by Huynh et al [ibid]. To determine whether expression of the fusion protein was under the control of the lac Z promoter, lysates of the recombinant lysogens were examined, by immunoblotting, after: 1) heat-induction at 45° C. followed by growth at 37° C. for 60 min. with 10 mM isopropyl β-d-thiogalactoside (IPTG); 2) heat induction following by growth at 30° C. without IPTG; and 3) growth at 32° C. in the presence of 10 mM IPTG.

Immunoblots of recombinant lysogens were examined for reactivity of the fusion protein with: 1) rabbit candidal antiserum (diluted 1:25 in 3% bovine serum albumin in buffered saline); 2) a monoclonal antibody to β-galactosidase, obtained commercially from Promega Biotec, Liverpool (1:5,000 dilution); and 3) sera (1:10) from patients with antibody to the 47 KD antigen, including five patients with AIDS and one patient recovering from systemic candidiasis who seroconverted to the 47 KD antigen; sera from five HIV antibody-positive patients with no evidence of candidiasis were used as controls.

DNA Sequencing and Analysis

Restriction enzyme mapping inserts from the five positive clones identified an overlapping region, suggesting that the epitopes expressed by each clone were encoded by a single genomic segment. This region from clone CA-1, extending 2 KB from the 5' termini of the insert, was subcloned into the EcoRI site of pUC19. It was sequenced by the dideoxy chain termination method of Sanger et al [Proc. Natn. Acad. Sci. USA 74 5463–5467 (1977)]. Reading frame analysis revealed a single open reading frame (CA-orf) extending from the EcoRI cloning site. The FASTA programme [Pearson, W. R. and Lipman, D. J., Proc. Natn. Acad. Sci. USA, 85, 2444–2448, (1988)] was used to compare the predicted polypeptide with the PIR protein database.

RESULTS

Figure 2A:
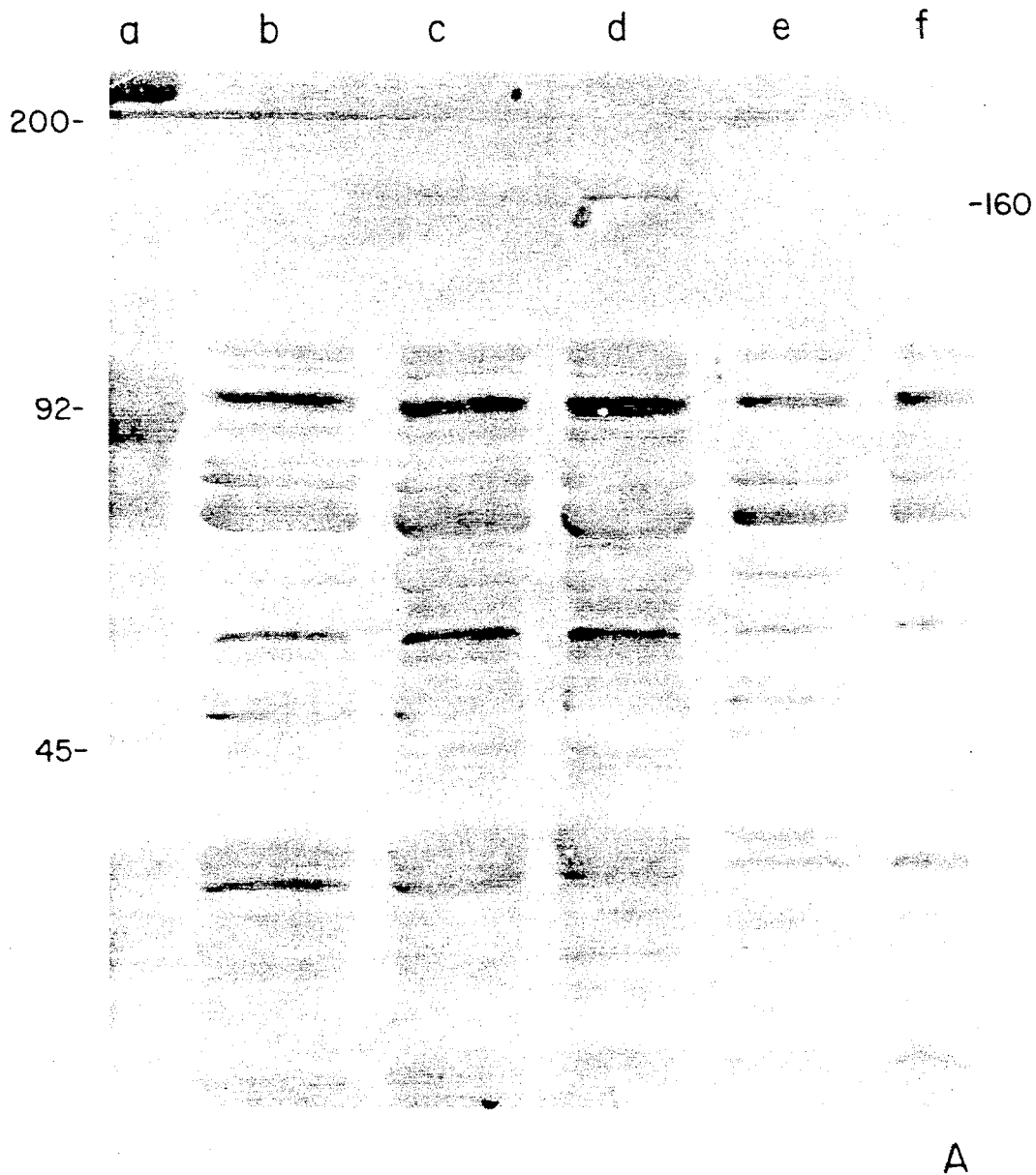
FIG. 2A shows immunoblots of recombinant lysogen prepared from clone CA-1.
Figure 2B:
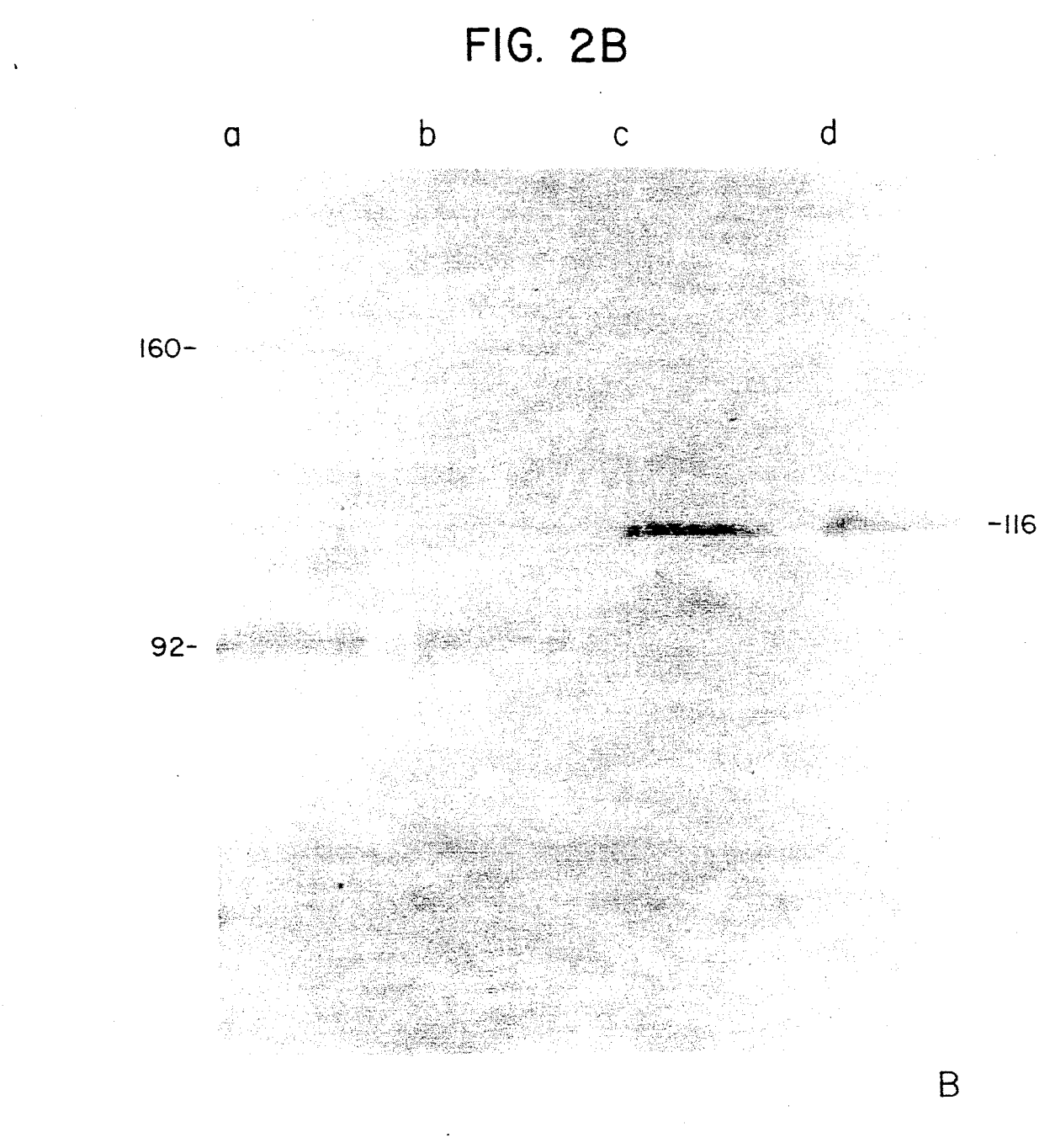

All five clones expressed epitopes which cross-reacted with the 47 KD antigen and a 92 KD antigen of C. albicans (FIG. 1). Immunoblots of recombinant lysogens, grown with and without IPTG, demonstrated that expression was under the regulation of the lac promoter (FIG. 2A). The cloned antigen was fused to β-galactosidase. The fusion protein produced by clone CA-1 had an elevated molecular weight, Mr 160 KD, compared to native β-galactosidase (Mr 116 KD) (FIG. 2B). A lower Mr band was also seen reacting with the anti-galactosidase monoclonal antibody, indicating the fusion protein was inherently less stable than native β-galactosidase.

Figure 2C:
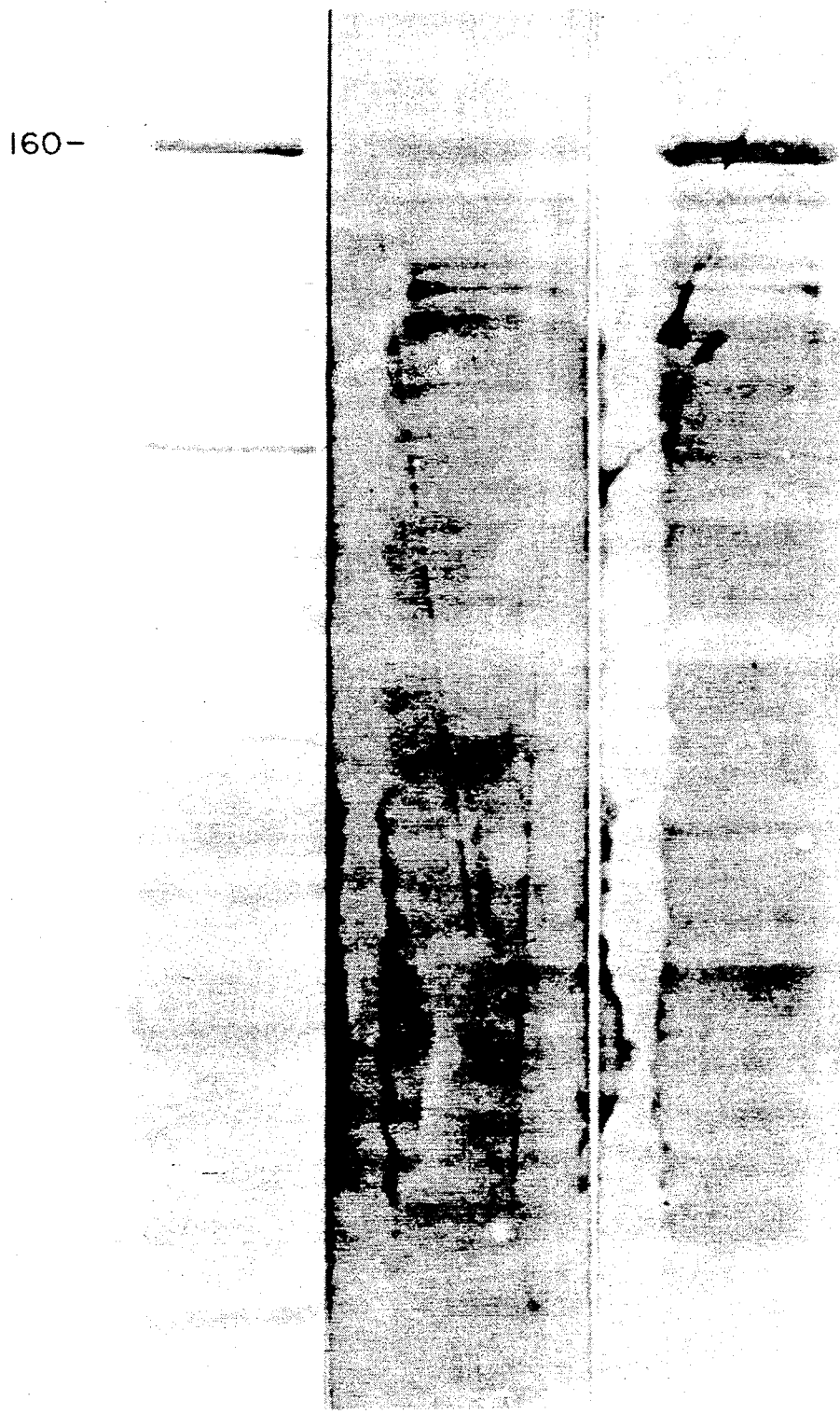
FIG. 2C shows immunoblots of recombinant lysogen CA-1 probed with sera from patients having antibody to the 47 Kd antigen.

As well as the rabbit candidal antiserum, the fusion protein also reacted with sera from AIDS patients with antibody to the 47 KD antigen, but not HIV antibody positive patients without this antibody. A patient with systemic candidiasis who seroconverted to the 47 KD antigen also seroconverted to the fusion protein (FIG. 2C). The patients' sera, which had not been absorbed with E. coli, reacted with several other bands in the recombinant lysogens and the λgt 11 control, and therefore these bands were considered to be E. coli antigens.

Nucleotide analysis of the insert DNA from clone CA-1 revealed a single partial open reading frame (orf) which continued in from the cloning site and coded for a polypeptide of 395 amino acids (Mr 45 KD). This orf was in phase with the β-galactosidase gene. Since fusion with β-galactosidase (Mr 116 KD) results in removal of the C-terminal 19 residues from the lac Z gene, the calculated size of the fusion protein was 159 KD. This agrees with the estimated value of 160 KD for the fusion protein produced by clone CA-1.

A database search, with the polypeptide sequence derived from this orf, revealed significant (>45%) homologies with heat shock proteins (hsps) from Drosophila [Blackman, R. K. and Meselson, M. (1986) J. Mol. Biol. 188, 499–515] and chickens [Kulomaa, M.S., et al (1986) Biochemistry 25, 6244–6251] and microsomal glucose-regulated proteins (grps) from hamsters [Sorger, P. K. and Pelham, H. R. B., (1987) J. Mol. Biol. 194, 341–344] and mice [Smith, M. J. and Koch, G. L. E., (1987) J. Mol. Biol. 194, 345–347]. The most extensive sequence similarity was found with the yeast hsp 90 protein of Saccharomyces cerevisiae [Farrelly, F. W. and Finkelstein, D. B. (1984) J. Biol. Chem. 259, 5745–5751], with 83.5% identity in the 395 amino acid overlap (FIG. 3).

The following figures are referred to above. In the figures:

FIG. 1 shows immunoblots of C.albicans probed with: antigen-selected antibodies from two of the positive clones showing cross-reactivity with the 92 KD and 47 KD antigens, and weakly, two intermediate components (tracks a and b); negative control elnate from non-recombinant plaques (c); rabbit candidal antiserum (d); AIDS patient's serum containing high titre antibody to the 47 KD antigen (e).

FIG. 2A shows immunoblots of recombinant lysogen prepared from clone CA-1, probed with rabbit candidal antiserum, showing the 160 KD fusion protein is present when heat induction at 45° C. is followed by growth at 37° C. for 60 min. with 10 mM IPTG (tracks c and d, showing two different lysogenic preparations). It is not produced when lysogens are grown at 32° C. (track b) or heat-induced but grown without IPTG (tracks e and f). Molecular weight markers (KD) shown in track a.

FIG. 2B shows immunoblots of recombinant lysogen CA-1 probed with monoclonal antibody against β-galactosidase. The 160 KD fusion protein and breakdown product are shown after growth with IPTG (track a), and without IPTG (track b); a non-recombinant λgt11 lysogen, grown with and without IPTG shows the position of native β-galactosidase (Mr 116 KD) (tracks c and d).

FIG. 2C shows immunoblots of recombinant lysogen CA-1 probed with sera from patients having antibody to the 47 KD antigen. Serum from an AIDS patient with antibody to the 47 KD antigen cross-reacting with 160 KD fusion protein (track a); and early (b) and late (c) sera from a patient recovering from systemic candidiasis who seroconverted to the 47 KD antigen, showing seroconvertion to the 160 KD fusion protein.

FIG. 3 is a comparison of the predicted amino acid sequence of the C. albicans open reading frame (CA-orf) with S. cerevisae hsp90 (SCHS90). Over the CA-orf sequence they showed >83% direct homology (:) or >98% conserved homology (.).

EXAMPLE 2

The sequenced carboxy end of a Candida albicans stress protein according to the invention was epitope mapped using the method described by Geysen H. M. et al in Journal of Immunological Methods 102, 259–274 (1987).

Identification of sequential epitopes is readily accomplished using a complete set of all possible overlapping synthetic peptides of a given length homologous with the sequence of the antigen of interest. With the proviso that the length of the peptides is equal to or greater than the longest sequential epitope, ELISA testing of this set of peptides with a given serum specific for that antigen will identify the antibody-binding peptides defined by that serum. The relationship between the antibody-binding peptides and sequential epitopes of the antigen is then established by methods such as competitive inhibition of binding using the whole antigen, use of monospecific antibody preparations, and by demonstrating with sufficient appropriately chosen negative controls that the antibodies binding to the peptides are antigen-specific.

"It is likely that the only essential criterion for effective binding of antibody to a peptide is that complementarily between the antigen-combining site of the antibody and the molecular surface of the binding peptide is maintained in regard to both shape and charge. It follows that antibody binding peptides deduced without recourse to sequence information should be defined as 'mimotopes', or mimics of the epitope which induced the antibody, rather than assuming that they are an accurate reproduction of that epitope.

"With the demonstration that antibodies bind to dipeptides in a reproducible manner and with a high degree of specificity (Geysen, 1985), it seemed likely that a strongly binding peptide could be built up from the optimum dipeptide binding unit . . . In order to extend a selected, strongly binding dipeptide to give a mimotope of higher specificity and affinity, sets of longer peptides were synthesized. These 'extension sets' consisted of approximately 184 peptides, comprising both the amino terminal and carboxy terminal addition to the dipeptide of members of a set of diverse amino acids, with or without the insertion of β-alanine as a spacer. The set of amino acids comprised the L- and D-isomers of each genetically coded amino acid, and a small selection of amino acids which do not occur in proteins."

This technique involves the synthesis of large numbers of overlapping peptides and identifies continuous antigenic peptides on a protein antigen. It will not detect carbohydrate or discontinuous epitopes. By way of example further details of two of these epitopes are given below:

1. STDEPAGESA

This epitope occurs just before the carboxy terminal 5 amino acid residues of the sequence of formula (1). It reacted with: (1) hyperimmune sera from 2 out of 3 rabbits immunised with Candida albicans pressate [as described in Burnie J. P., et al J. Clin. Pathol. 38, 701–706 (1985)]; (2) sera from 3 out of 5 patients with systemic candidiasis, two of whom seroconverted to this epitope; (3) pooled sera from 4 patients who were HIV antibody positive [who have antibody to the 47 Kd antigen—see Matthews R. C., et al Lancet ii; 263–266 (1988)]. It did not react with sera from 7 normal control patients or a patient with chronic mucocutaneous candidiasis (CMC).

This epitope was synthesised and conjugated to keyhole limpet haemocyanin (KLH) via the terminal cysteine to give KLH-Cys-STDEPAGESA. A rabbit polyclonal antiserum raised against this, on immunoblotting against Candida albicans, recognised a heat-inducible antigen at about 92 Kd (present AT 37° C. but not 23° C.) and a constitutive antigen at about 40 Kd (present when grown at 23° C. or 37° C.). It did not detect the 47 Kd antigen. It did not cross-react with S-cerevisiae or Aspergillus fumigatus.

2. LSREM-LKVIRK

These two epitopes are situated close to each other, 316-332 amino acid residues from the carboxy end of the sequence of formula (1). The LSREM epitope reacted with; (1) 2 out of 3 rabbit hyperimmune candidal antisera; (2) 4 out of 5 sera from patients with systemic candidiasis, one of whom seroconverted to it; (3) pooled sera from 4 HIV antibody positive patients and (4) serum from the CMC patient. It did not react with sera from 7 negative control patients. A rabbit immunised with KLH-Cys-LPLNLSREML failed to produce antibody to it.

Figure 4:
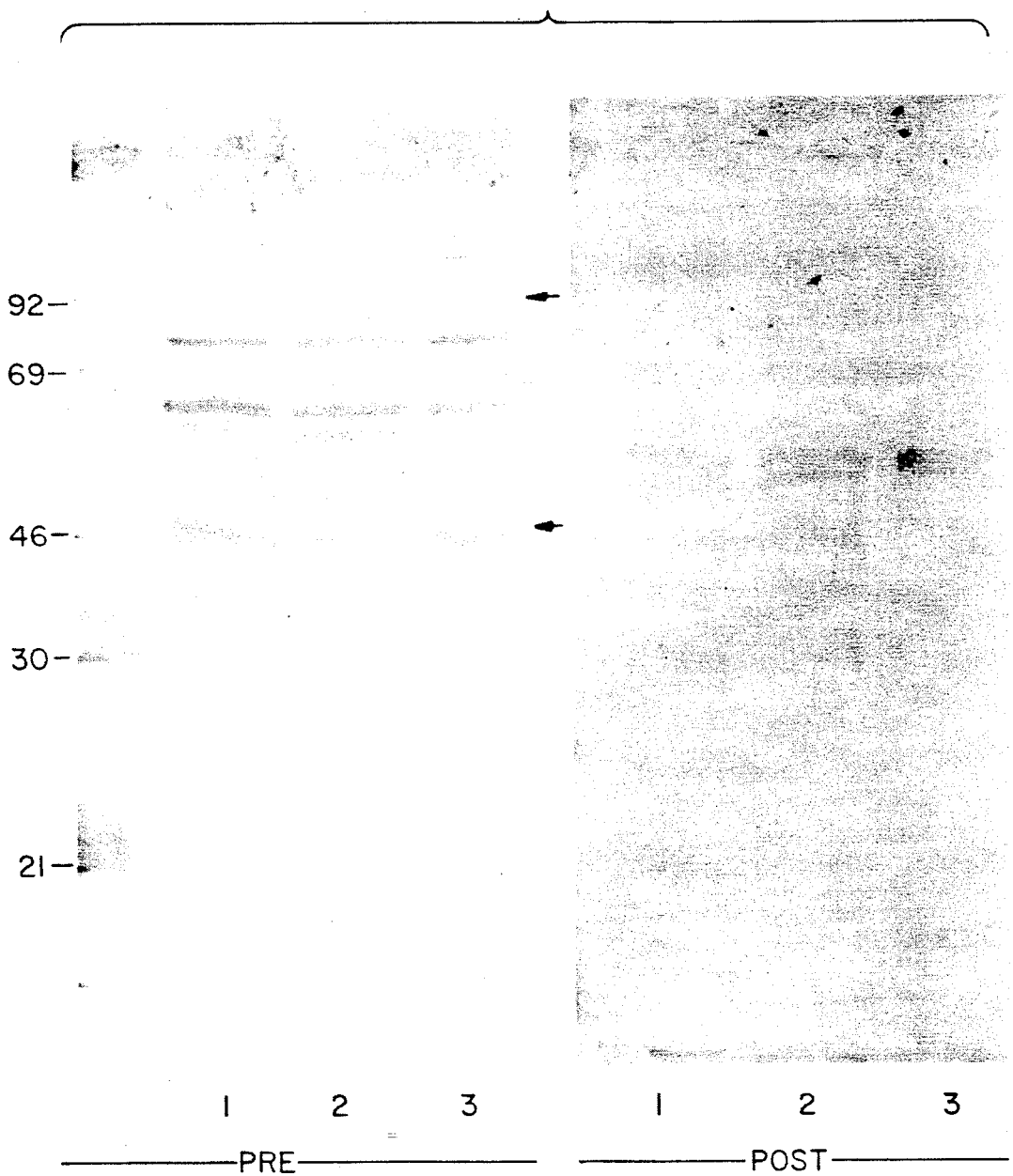
FIG. 4 shows immunoblots of *C.albicans* in the yeast phase probed with rabbit antiserum raised against LKVJRKNIVKKMIE-Cys-KLH.
Figure 5:
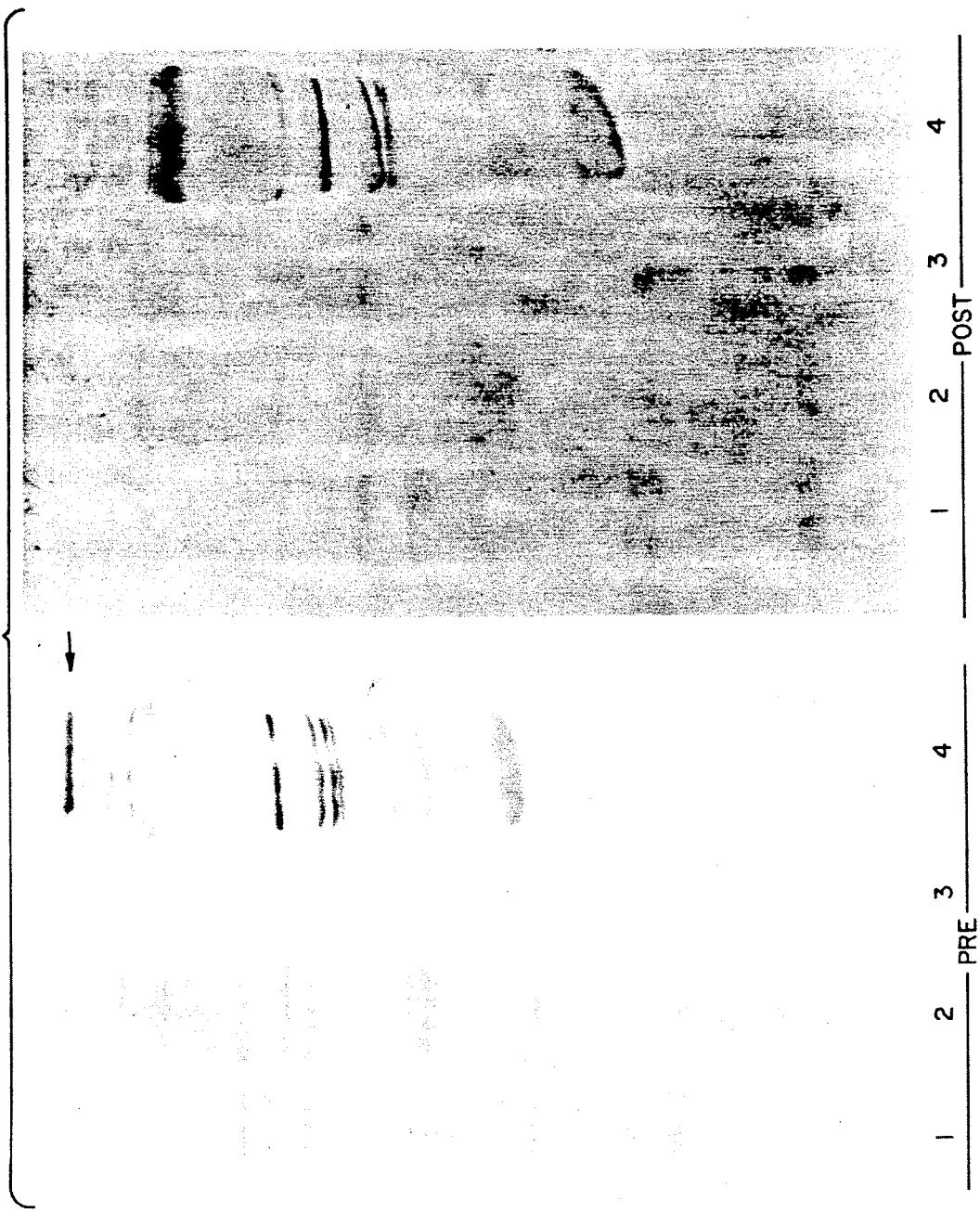
FIG. 5 shows immunoblots of *C.albicans* in the mycelial phase probed with rabbit antiserum raised against LKVIRKNIVKKMIE-Cys-KLH.

The LKVIRK epitope was specifically detected by infected patients' sera. None of the hyperimmune rabbit sera recognised it nor any of the 7 negative control patients. All five patients with systemic candidiasis had antibody to this epitope and in two case, where serial sera were available, seroconverted to it. The pooled sera from 4 HIV antibody positive patients and the patient with CMC also recognised this epitope. A rabbit polyclonal antiserum raised against the epitope (LKVIRKNIVKKMIE-Cys-KLH) recognised both the 47 Kd antigen and the antigen of about 92 Kd on immunoblots of various strains of C.albicans (including serotypes A and B) in both the yeast and mycelial phase (FIGS. 4 and 5). It also recognised the fusion protein produced by a positive clone. Cross-absorption with the synthesised peptide epitope removed this antibody activity. The antibody also recognised antigens on immunoblots of (1) Candida parapsilosis—giving a band at about 52 Kd (an antigen of this size was previously reported by Belder M. A., et al European heart Journal 10, 858–862 [1989]); (2) A. fumigatus—giving bands at about 88 Kd, 51 Kd and 40 Kd [these antigens have previously been reported, Matthews R. C., et al J. Clin. Pathol. 38, 1300–1303 (1985)] and (3) S.cerevisiae—at about 84 Kd and 45 Kd, compatible with S. cerevisiae hsp 90. This therefore suggests the presence of a stress protein according to the invention in A. fumigatus of about 88 Kd.

In FIGS. 4 and 5 referred to above, the following is shown:

FIG. 4 shows immunoblots of C.albicans in the yeast phase probed with rabbit antiserum raised against LKVIRKNIVKKMIE-Cys-KLH both before (PRE) and after (POST) cross-absorption with this peptide. Molecular weight markers shown on left hand side. Lane number 1, outbreak strain of C.albicans [Burnie J. P., et al B. M. J. 290, 746-748 (1985)]; lane no. 2, C.albicans strain NCTC3153 (serotype A); lane no. 3, C.albicans strain NCTC3156 (serotype B). The 47 Kd antigen and the antigen at about 92 Kd are arrowed. Notice these antigens are missing after cross-absorption.

FIG. 5 Lanes 1-3 are as in FIG. 5 but with the yeast in the mycelial phase. Probed with the same antiserum as in FIG. 4, pre and post cross-absorption with the peptide. Lane no. 4 is a positive clone showing the fusion protein disappearing after cross-absorption, as do the 47 Kd and 92 Kd antigens in lanes no. 1-3.

Antibody raised against the peptide STDEPAGESA or LKVIRKNIVKKMIE was used to examine the sera of patients with systemic candidiasis as follows:

Antigen was detected by dot-blotting serum directly onto nictrocellulose membrane. Briefly, 100 μl of antiserum was loaded into each well of a Bio-Dot microfiltration apparatus (Biorad laboratories). This had been previously loaded with a sheet of nitrocellulose membrane prewashed in pH 7.5 Tris buffered saline (TBS). The sample was allowed to drain through under gravity. Each well was loaded with a further 100 μl of TBS which drains under gravity control. This is followed by 2×100 μl TBS drained by vacuum. The membrane was then blocked in 3% BSA in TBS at 4° C. overnight. In the morning it was incubated with 30 μl of the appropriate rabbit serum in 3% BSA in TBS for 2 hours at room temperature. It was then washed in 20 mM Tris, 500 mM NaCl, 0.05% Tween 20, pH 7.5 for 30 minutes and incubated with alkaline phosphatase conjugated antirabbit (1:1000) (Sigma) for 1 hour at room temperature. It was washed again and stained for 15 minutes at room temperature in a freshly prepared and filtered mixture of equal volumes of naphthol AS-MX phosphate (Sigma; 0.4 mg/ml in distilled water) and fast red TR salt (Sigma; 6 mg/ml in 0.2M Tris, pH 8.2). Antibody intensity was compared by eye with that of controls whose density had been measured previously with a Joyce Loebl scanning densitometer. The results were classified as positive or trace according to the criteria of Matthews, R. C. and Burnie, J. P. (J. Clin. Micro., 26: 459-463 (1988).

Three groups of sera were examined. The Control sera came from patients who had been screened for systemic candidiasis but where there was no clinical or cultural evidence for the infection. The second group was patients who were colonized at clinically significant sites (intravenous lines, wound, faeces, urine and vagina) and where there was no evidence of dissemination. The third group consisted of either suspected or proven cases. In the suspected cases a clinically significant pyrexia resolved on systemic amphotericin B therapy. The patients were neutropenic and although some cultures were positive for Candida albicans this was insufficient to prove the infection. In the proven cases there was either cultural and histological evidence from a deep site at autopsy or two sets of positive blood cultures taken from separate sites on two different occasions during life.

The sera were examined against antibody raised against the peptide STDEPAGESA or the peptide LKVIRKNIVKKMIE. The former detected (trace or positive response) 90.4% of cases. The latter detected 88.2% of proven and all the suspected cases. There was also a positive response in four patients where a localised infection required treatment with systemic amphotericin B. Both antibodies detected circulating candidal antigen specific to disseminated candidiasis.

| Results of Dot-Blotting | | | |
|---|---|---|---|
| | Nil | Trace | Positive |
| 1. Antibody against STDEPAGESA | | | |
| Controls | 65 | | |
| Colonized | 6 | 1 | |
| Systemically infected (proven) | 2 | 8 | 11 |
| 2. Antibody against LKVIRKNIVKKMIE | | | |
| Controls | 404 | | |
| Colonized | 10 | 5 | 4[a] |
| Systemically infected | | | |
| (proven) | 6 | 9 | 36 |
| (suspected) | | 4 | 6 |

[a]required systemic therapy for N line infection (1), urinary tract infection (2) and wound infection (1) with amphotericin B.

EXAMPLE 3

A murine monoclonal antibody was raised against LKVIRKNIVKKMIE-Cys-KLH (see Example 2). Balb/c and CBA x Balb/c F1 mice were injected subcutaneously with 50 μg of immunogen in sterile complete Freund's Adjuvant and thereafter at intervals of 14 days, intraperitoneally with 50 μg immunogen in Incomplete Freund's Adjuvant until seroconvertion.

Fusion was performed 4 days after a final immunisation of 50 μg immunogen intravenously in sterile physiological saline. Fusion, hybridoma screening, clonal selection and antibody analysis were performed according to standard protocols, essentially as described by de St. Groth S. F. and Scheidegger D., J. Immunol. Methods 35, 1-21 (1980). Selected hybridomas were screened for activity against the C.albicans 47 Kd antigen by immunoblotting against C.albicans. Positive hybridomas were re-cloned and re-assayed.

A novel hybridoma cell line (CA-STR7-1) was produced which recognised both the C.albicans 47 Kd antigen and the antigen of approximately 92 Kd on immunoblots of C.albicans grown at 37° C., in both the yeast and mycelial forms. At 23° C. the 47 Kd antigen was visible but not the 92 Kd antigen with this monoclonal antibody.

EXAMPLE 4

A monoclonal antibody was raised against the peptide STDEPAGESA using the method of Example 3, and was used in a mouse model to determine whether it had a protective effect against challenge with a lethal dose of C.albicans. The mouse model was as follows:

Male Balb C mice of average weight 2.5 g were injected i.v. with dilutions of a standardised batch of frozen C.albicans. The injected volume was 100 μl via the lateral tail vein. The following mortality was observed at the doses and times shown:

| | Mortality at | | |
|---|---|---|---|
| Dose | 18 hrs | 24 hrs | n |
| 5 × 10⁸ cells | 89% | 100% | 54 |
| 1 × 10⁸ cells | 76% | 100% | 48 |
| 5 × 10⁷ cells | 0% | 0% | 24 |

The viability of injected cells from frozen aliquats was 30% and therefore the dose could be adjusted downwards.

A challenge dose of 1×10⁸ C.albicans cells was used as described above in mice which had been pre-treated with the antibody against STDEPAGESA by prior injection as follows:

| | | Mortality at | | "Protective" Agent |
|---|---|---|---|---|
| | n | 24 hrs | 48 hrs | injected volume |
| STDEPAGESA Mab | 6 | 66% | 83.3% | 0.2 ml 1 hr prior to challenge |
| Mab L2 | 6 | 100% | — | 0.2 ml 1 hr prior to challenge |
| Patient 1 | 6 | 50% | 50% | 0.5 ml 30 min prior to challenge |
| Patient 2 | 7 | 42.8% | 42.8% | 0.5 ml 30 min prior to challenge |
| | 5 | 40% | 40% | 0.5 ml 30 min prior to challenge |
| Normal Human Serum | 6 | 100% | — | 0.5 ml 30 min prior to challenge |
| IG fraction Patient 2 | 6 | 50% | 66% | 0.5 ml 30 min prior to challenge |
| IG fraction normal human serum | 6 | 100% | — | 0.5 ml 30 min prior to challenge |

"Patient 1" and "Patient 2" was serum from patients who developed systemic Canidida infections, developed an antibody response and recovered.
"IG fraction" was an immunoglobulin fraction obtained by 50% ammonium sulphate precipitation, dialysed overnight v PBS and resuspended in the same volume as the original serum.
Mab L2 was an irrelevant IgG antibody.

CONCLUSION

The monoclonal antibody raised against STDEPAGESA produced 33% survival at 24 hrs in animals challenged with a lethal dose of C.albicans, whereas the irrelevant IgG and normal human serum produced no protection. The serum from the previously infected patients produced 55% protection at 24 hrs.

We claim:

1. A purified candidal stress protein having an amino acid sequence which includes at least the sequence of FIG. 3:

```
           10         20         30
        EFRAILFVPKRAPFDAFESKKKKNNIKLYV
                40         50         60
             RRVFITDDAEELIPEWLSFIKGVVDSEDLP 70         80         90
        LNLSREMLQQNKILKVIRKNIVKKMIEIFN
                100        110        120
             EISEDQEQFNQFYTAFSKNIKLGIHEDAQN 130        140        150
        RQSLAKLLRFYSTKSSEEMTSLSDYVTRMP
                160        170        180
             EHQKNIYYITGESIKAVEKSPFLDALKAKN 190        200        210
        FEVLFMVDPIDEYAMTQLKEFEDKKLVDIT
                220        230        240
             KDFELEESDEEKAAREKEIKEYEPLTKALK 250        260        270
        DILGDQVEKVVVSYKLVDAPAAIRTGQFGW
                280        290        300
             SANMERIMKAQALRDTTMSSYMSSKKTFEI 310        320        330
        SPSSPIIKELKKKVETDGAEDKTVKDLTTL
                340        350        360
             LFDTALLTSGFTLDEPSNFAHRINRLIALG 370        380        390
        LNIDDDSEETAVEPEATTTASTDEPAGESAMEEVD*
``` or immunogenic epitope thereof or a candidal homolog thereof, wherein antibodies that detect said protein, epitope or homolog cross react with the *Candida albicans* 47 kilodalton antigen or its 92 kilodalton precursor which comprises the sequence of FIG. 3.

2. An immunogenic epitope of a candidal stress protein comprising the sequence STDEPAGESA, LSREM, KILK, LKVIRK or LKVIRKNIVKKMIE.

3. The epitope according to claim 2 wherein said stress protein includes the sequence of FIG. 3.

```
           10         20         30
        EFRAILFVPKRAPFDAFESKKKKNNIKLYV
                40         50         60
             RRVFITDDAEELIPEWLSFIKGVVDSEDLP 70         80         90
        LNLSREMLQQNKILKVIRKNIVKKMIEIFN
                100        110        120
             EISEDQEQFNQFYTAFSKNIKLGIHEDAQN 130        140        150
        RQSLAKLLRFYSTKSSEEMTSLSDYVTRMP
                160        170        180
             EHQKNIYYITGESIKAVEKSPFLDALKAKN 190        200        210
        FEVLFMVDPIDEYAMTQLKEFEDKKLVDIT
                220        230        240
             KDFELEESDEEKAAREKEIKEYEPLTKALK 250        260        270
        DILGDQVEKVVVSYKLVDAPAAIRTGQFGW
                280        290        300
             SANMERIMKAQALRDTTMSSYMSSKKTFEI 310        320        330
        SPSSPIIKELKKKVETDGAEDKTVKDLTTL
                340        350        360
             LFDTALLTSGFTLDEPSNFAHRINRLIALG 370        380        390
        LNIDDDSEETAVEPEATTTASTDEPAGESAMEEVD*.
```

4. An isolated DNA sequence coding for a fungal stress protein comprising substantially the nucleotide sequence:

```
GAATTCAGAGCTATCTTGTTTGTTCCAAAGAGAGCTCCATTTGATGCCTTTGAATCCAAG
      10        20        30        40        50        60

AAGAAGAAGAACAACATCAAATTATACGTCCGTAGAGTGTTTATCACTGATGATGCTGAA
      70        80        90       100       110       120

GAGTTGAATCCAGAATGGTTAAGTTTCATCAAGGGGGTTGTCGATTCCGAAGACTTGCCA
     130       140       150       160       170       180

TTGAACTTGTCCAGAGAAATGTTGCAACAAAACAAGATTTTGAAAGTTATCAGAAAGAAC
     190       200       210       220       230       240

ATTGTCAAAAAGATGATTGAAACTTTCAATGAAATCTCTGAAGACCAAGAGCAATTCAAC
     250       260       270       280       290       300

CAATTCTACACTGCTTTCTCCAAGAACAYCAAAYYHHHYAYYCAYHAAHAYHCYCAAAAC
     310       320       330       340       350       360

AGACAATCTTTGGCTAAATTGTTGAGATTCTACTCTACCAAATCTTCTGAAGAAATGACT
     370       380       390       400       410       420

TCCTTGTCTGACTACGTTACTAGAATGCCAGAACACCAAAAGAATATCTACTACATCACT
     430       440       450       460       470       480
```

-continued

```
GGTGAATCCATCAAAGCCGTTGAAAAATCACCATTCTTGGATGCCTTGAAAGCTAAGAAC
   490       500       510       520       530       540

TTTGAAGTCTTGTTCATGGTGGATCCAATCGATGAATATGCCATGACTCAATTGAAGGAA
   550       560       570       580       590       600

TTTGAAGACAAGAAATTGGTTGATATTACCAAAGACTTTGAATTGGAAGAAAGTGACGAA
   610       620       630       640       650       660

GAAAAGCTGCTAGAGAAAAGGAAATCAAAGAATACGAACCATTGACCAAAGCTTTGAAA
   670       680       690       700       710       720

GATATTCTTGGTGSTCAAGTTGAAAAAGTTGTTGTTTCCTACAAACTTGTTGATGCTCCA
   730       740       750.      760       770       780

GCTGCCATTSGAACTGGTCAATTTGGTTGGTCTGCCAATATGGAAAGAATCATGAAGGCT
   790       800       810       820       830       840

CAAGCTTTGAGAGACACCACCATGTCTTCTTACATGTCCTCTAAGAAGACCTTTGAAATT
   850       860       870       880       890       900

TCTCCATCTTCCCCAATTATCAAGGAATTCAAGAAGAAAGTTGAAACCGATGGAGCTGAA
   910       920       930       940       950       960

GACAAGACCGTTAAGGACTTGACCACTTTGTTGTTTGATACTGCATTGTTGACTTCTGGT
   970       980       990      1000      1010      1020

TTCACCTTGGACGAACCATCCAACTTTGCCCACAGAATTAACAGATTGATTGCCTTGGGA
  1030      1040      1050      1060      1070      1080

TTGAATATTGACGATGATTCAGAAGAAACTGCTATTGAACCTGAAGCTACTACTACTGCC
  1090      1100      1110      1120      1130      1140

TCAACTGACGAACCAGCTGGAGAATCTGCTATGGAAGAAGTTGATTAAACACCAGAAGGG
  1150      1160      1170      1180      1190      1200.
```

5. An expression vector including the DNA sequence according to claim 4 operably linked to a promoter.

6. An immunogen comprising a purified candidal stress protein or fragment thereof, wherein antibodies that detect said protein or fragment cross-react with the *Candida albicans* 47 kilodalton antigen or its 92 kilodalton precursor which comprises the sequence of FIG. 3.

7. A purified candidal stress protein having an amino acid sequence which includes at least the sequence of formula (1):

```
         10         20         30
      EFRAILFVPKRAPFDAFESKKKKNNIKLYV 40         50         60
              RRVFITDDAEELIPEWLSFIKGVVDSEDLP 70         80         90
      LNLSREMLQQNKILKVIRKNIVKKMIEIFN 100        110        120
              EISEDQEQFNQFYTAFSKNIKLGIHEDAQN 130        140        150
      RQSLAKLLRFYSTKSSEEMTSLSDYVTRMP 160        170        180
              EHQKNIYYITGESIKAVEKSPFLDALKAKN 190        200        210
      FEVLFMVDPIDEYAMTQLKEFEDKKLVDIT 220        230        240
              KDFELEESDEEKAAREKEIKEYEPLTKALK 250        260        270
      DILGDQVEKVVVSYKLVDAPAAIRTGQFGW 280        290        300
              SANMERIMKAQALRDTTMSSYMSSKKTFEI 310        320        330
      SPSSPIIKELKKKVETDGAEDKTVKDLTTL 340        350        360
              LFDTALLTSGFTLDEPSNFAHRINRLIALG 370        380        390
      LNIDDDSEETAVEPEATTTASTDEPAGESAMEEVD*.
```

8. A method of making an epitope that is immunologically equivalent to a parent epitope that has the sequence STDEPAGESA, LSREM, KILK, LKVIRK, or LKVIRKNIVKKMIE, said equivalent epitope having structure such that antibodies that detect said equivalent epitope cross react with the *Candida albicans* 47 kilodalton antigen or its 92 kilodalton precursor which comprises the sequence of FIG. 3, wherein said method comprises:

i) synthesizing a complete set of oligopeptide analogs, each analog differing from said patent epitope at a single amino acid residue;

ii) comparing the reactivity of each of said analogs with antibody which detects said parent epitope and thereby determining which of said amino acids is essential for reactivity with said antibody and which is replaceable; and iii) synthesizing said immunologically equivalent epitope that differs in amino acid sequence from said parent epitope by one or more amino acid.

9. A mimotope of STDEPAGESA, LSREM, KILK, LKVIRK, or LKVIRKNIVKKMIE, wherein antibodies that detect said mimotope cross-react with the *Can-* dida albicans 47 kilodalton antigen which comprises the sequence of FIG. 3.

10. A fragment of a candidal stress protein comprising the sequence STDEPAGESA, LSREM, KILK, LKVIRK, or LKVIRKNIVKKMIE, wherein antibodies that detect said fragment cross react with the Candida albicans 47 kilodalton antigen or its 92 kilodalton precursor which comprises the sequence of FIG. 3.

11. A purified candidal stress protein according to claim 1 obtained from an isolate of *Candida albicans, Candida parapsilosis, Candida krusei*, or *Candida tropicalis*.

* * * * *